US008629080B2

(12) United States Patent
Bourane et al.

(10) Patent No.: US 8,629,080 B2
(45) Date of Patent: Jan. 14, 2014

(54) HYDRATED NIOBIUM OXIDE NANOPARTICLE CONTAINING CATALYSTS FOR OLEFIN HYDRATION

(75) Inventors: Abdennour Bourane, Ras Tanura (SA); Stephan Ralf Vogel, Dhahran (SA); Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 470 days.

(21) Appl. No.: 13/052,812

(22) Filed: Mar. 21, 2011

(65) Prior Publication Data

US 2012/0245397 A1  Sep. 27, 2012

(51) Int. Cl.
*B01J 23/20* (2006.01)
*C07C 29/04* (2006.01)

(52) U.S. Cl.
USPC ............ 502/353; 502/208; 502/217; 568/896

(58) Field of Classification Search
USPC ........................... 502/353, 208, 217; 568/896
See application file for complete search history.

(56) References Cited

U.S. PATENT DOCUMENTS

| | | | |
|---|---|---|---|
| 2,477,380 | A | 7/1949 | Kreps et al. |
| 3,452,106 | A | 6/1969 | Sato et al. |
| 4,065,512 | A | 12/1977 | Cares |
| 4,154,580 | A | 5/1979 | Landis |
| 4,214,107 | A | 7/1980 | Chang et al. |
| 4,376,732 | A | 3/1983 | Ramirez |
| 4,477,591 | A | 10/1984 | Ramirez |
| 4,499,313 | A | 2/1985 | Okumura et al. |
| 4,579,984 | A | 4/1986 | Neier et al. |
| 4,652,544 | A | 3/1987 | Okazaki et al. |
| 4,927,931 | A | 5/1990 | Molzahn et al. |
| 5,449,852 | A | 9/1995 | Chauvin et al. |
| 5,593,936 | A | 1/1997 | Glock et al. |
| 5,616,815 | A | 4/1997 | Atkins |
| 5,684,216 | A | 11/1997 | Haining |
| 5,919,963 | A | 7/1999 | Hochido et al. |
| 6,036,880 | A | 3/2000 | Komada et al. |
| 6,432,858 | B1 | 8/2002 | Tezuka |
| 7,276,225 | B2 | 10/2007 | Brown et al. |
| 2003/0082097 | A1 | 5/2003 | Brown et al. |
| 2005/0225927 | A1 | 10/2005 | Tagusagawa et al. |
| 2006/0102519 | A1 | 5/2006 | Tonkovich et al. |
| 2007/0256736 | A1 | 11/2007 | Tonkovich et al. |
| 2008/0194400 | A1 | 8/2008 | Schmidt |
| 2010/0081726 | A1 | 4/2010 | Tonkovich et al. |
| 2010/0210454 | A1 | 8/2010 | Epshteyn et al. |

FOREIGN PATENT DOCUMENTS

| | | |
|---|---|---|
| DE | 102004052696 A1 | 5/2006 |
| EP | 0135145 A2 | 3/1985 |
| EP | 0173189 A2 | 3/1986 |
| EP | 0323268 A2 | 7/1989 |
| JP | 2001079395 A | 3/2001 |

OTHER PUBLICATIONS

International Search Report and Written Opinion Issued in PCT/US2012/029929, dated Jul. 5, 2012 (20 pages).
English Patent Abstract of JP2001079395 from Patent Abstracts of Japan, Publication date Mar. 27, 2001 (1 page).
Machine-generated English Patent Abstract of DE102004052696 from espacenet.com, Publication date May 4, 2006 (1 page).
Tanabe K. et al, "Various reactions catalyzed by niobium compounds and materials", Applied Catalysis A: General, vol. 133 (Dec. 21, 1995) pp. 191-218, Elsevier Science B.V.
De Pietre M. K. et al., "H3P04- and H2S04—treated niobic acid as heterogeneous catalyst for methyl ester production", Reaction Kinetics and and Catalysis Letters, vol. 99 No. 2, (Jan. 13, 2010) pp. 269-280, Springer Science & Business Media.
Sumiya S. et al., "Facile preparation of SBA-15-supported niobic acid (Nb2O5.nH2o) catalyst and its catalytic activity", Applied Catalyst A: General, vol. 365 No. 2, (Aug. 31, 2009) pp. 261-267 Elsevier Science B.V.
Li Yingcheng et al., "Solid acid hydration catalyst for converting ethylene oxide to ethylene glycol", CA (Apr. 12, 2007), published under XP002411502 (1 page).
Ross, Julian R.H. et al., "The use of niobia in oxidation catalysis", Catalysis Today, 16 (1993) pp. 503-511, Elsevier Science Publishers B.V., Amsterdam.

*Primary Examiner* — Elvis O Price
(74) *Attorney, Agent, or Firm* — Bracewell & Giuliani LLP; Constance Rhebergen

(57) ABSTRACT

An olefin hydration catalyst and method for producing same is provided. The olefin hydration catalyst can be prepared by contacting a niobium containing compound with a strong Bronsted acid, such as sulfuric or phosphoric acid, to produce niobium oxo sulfate or niobium oxo phosphate nanoparticles. The nanoparticles can be separated, dried and utilized in a reactor for the hydration of olefins to their corresponding alcohols.

18 Claims, No Drawings

HYDRATED NIOBIUM OXIDE NANOPARTICLE CONTAINING CATALYSTS FOR OLEFIN HYDRATION

FIELD OF THE INVENTION

This invention relates to a catalyst and method of preparing a catalyst for olefin hydration. More specifically, the present invention relates to a catalyst and method of preparing a catalyst, wherein the catalyst includes amorphous or crystalline nanoparticles of hydrated niobium oxide, niobium oxo sulfate, niobium oxo-phosphate, or mixtures thereof, for use in the hydration of olefins.

BACKGROUND OF THE INVENTION

Alcohols find use in a variety of chemical processes. The hydration of alkenes to alcohols, such as the hydration of butene to butanol, is a commercially important reaction as the reaction products find several important industrial applications. For example, butanol can be used as a solvent or chemical intermediate for the productions of corresponding ketones, esters, and ethers, as well as being used for the preparation of a variety of other chemical compounds. In a similar fashion, other low molecular weight alkenes can be converted into corresponding low molecular weight alcohols for use as solvents or intermediates for the production of additional chemical compounds. Additionally, low molecular weight alcohols can also be used as additive or blending components for gasoline.

The hydration of alkenes to alcohols is typically an acid catalyzed reaction. The reaction typically requires relatively strong liquid Bronsted acids to achieve the desired reaction kinetics. Thus, the elimination of the use of strong Bronsted acids in olefin hydration is desirable.

For example, in one commercially practiced method for producing secondary butyl alcohols, a two-step process is employed wherein n-butenes are reacted with excess sulfuric acid (for example, 80%) to form the corresponding sulfate, which is then hydrolysed to sec-butanol, as follows:

$$C_4H_8 + H_2SO_4 \rightarrow C_4H_9OSO_3H \quad (1)$$

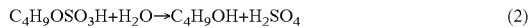

$$C_4H_9OSO_3H + H_2O \rightarrow C_4H_9OH + H_2SO_4 \quad (2)$$

During this process, the sulfuric acid becomes diluted to a concentration of about 35% by weight or less, and must then be re-concentrated before it can be recycled and used in the process. The process also has additional problems associated with the use of such liquid catalysts. Among these problems includes separation and recovery of the catalyst, corrosion of equipment and installations that come into contact with catalyst, and the formation of undesired byproducts, such as sec-butyl ether, isopropyl alcohol, various $C_5$-$C_8$ hydrocarbons, and polymers. In addition to reducing the overall yield of the reaction, some of these by-products also complicate the purification and recovery of the desired sec-butanol product.

In general, there are no solid acid catalysts suitable for use in the hydration of alcohols in the presence of water, except perhaps for certain ion exchange resins. Cationic exchange resins are known to offer substantial reaction rates in both polar and non-polar media. The use of cationic exchange resins that include sulfonated polystyrene resins cross-linked with divinyl benzene as catalysts for the hydration of olefins, such as propylene or butene, has been previously described in the literature (see, for example, U.S. Pat. Nos. 4,579,984 and 2,477,380; and the references cited therein). These exchange resins are believed to generally offer several process benefits, for example ease in separation of products and a non-corrosive environment. The use of these exchange resins, however, has certain limitations and many have not been found to be entirely satisfactory due, in part, to their leaching tendency, their limited range of application, and a general lack of the ability to regenerate and reuse the media.

Butanols have been identified as second generation biofuel component (i.e., biofuels obtained from non-food crops) after ethanol. The bio-route to produce such butanols, as an alternative to known methods for producing butanols, such as the hydration of olefins, has been previously reported, however, butanols that are produced through the bio-route are not efficient and the amount of butanols produced will not be enough to meet the demand of the butanol market. The production of butanols from propylene and carbon monoxide is costly and typically only produces n-butanol, which has relative low octane value as compared with the other butanol isomers. Thus, an effective and economical route to produce mixed butanols through olefin hydration is needed.

Although the olefin hydration has been studied extensively, one main objective of olefin hydration is to produce a single alcohol molecule, as opposed to a mixture of alcohols, to avoid complications associated with the separation thereof. When alcohols are utilized as fuel components, however, it is unnecessary to separate them out prior to use. Olefin hydration with strong Bronsted acids typically produces mixed alcohols product streams, and thus are useful as fuel components, but are not useful as intermediate chemicals.

As the direct catalytic hydration of alkenes to alcohols is an inexpensive route for preparing industrially useful alcohols, and a convenient synthetic route for the synthesis of secondary and tertiary alcohols in general, it is desirable to obtain solid catalysts for the reaction that are suitable for use in water.

SUMMARY

The current invention provides a catalyst and method for making the same for the hydration of olefins.

In one aspect, the present invention relates to an olefin hydration catalyst that includes niobium oxo sulfate or niobium oxo phosphate nanoparticles. In certain embodiments, the catalyst can include a support material and the nanoparticles can be impregnated or precipitated thereon.

In another aspect, a method for the preparation of the niobium oxo sulfate or niobium oxo phosphate nanoparticles is provided, the method including the steps of contacting a niobium containing compound with a Bronsted acid to precipitate a solid nanoparticle, removing excess liquid, and recovering a solid catalyst material.

In another aspect, a method for the hydration of an olefin to an alcohol is provided, the method including the steps of contacting an olefin feedstock with an olefin hydration catalyst that includes niobium based nanoparticles in a reaction zone for a contact time sufficient to convert at least a portion of the olefin present into an alcohol, withdrawing a product stream from said reaction zone, said product stream including an organic phase and an aqueous phase, the organic phase including the alcohol; and separating the organic phase to produce an alcohol product stream.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

In one aspect, this invention relates to a novel method for the hydration of olefins using catalysts that include amorphous hydrated niobium oxide nanoparticles. In certain embodiments, the present invention describes the olefin hydration catalyst and method for producing highly desirable mixed butanol based octane enhancers and oxygenates from inexpensive hydrocarbon feedstocks, such as from an FCC refinery propylene stream, gas plant off-gases (which can contain ethylene and/or propylene), naphtha off-gases (which can include olefins), FCC light gasoline stream (which can include pentenes, hexenes, and/or heptenes), or a product or off-gas stream from any other thermal cracking unit. The resulting octane enhancers and oxygenates can be added to other hydrocarbon products, such as gasoline.

In another aspect, the present invention relates to a catalyst for the hydration of olefins to produce alcohols, wherein the catalyst that includes amorphous hydrated niobium oxide nanoparticles. In certain embodiments, catalysts of the present invention can be prepared by the precipitation of a niobium salt or mixture thereof, for example ammonium niobate (V) oxalate, niobium (III) chloride 1,2-dimethoxyethante, potassium niobate, niobium (V) acetyl acetonate, niobium alkoxides (e.g., niobium ethoxide) or niobium halides (e.g., niobium pentachloride), in a strong Bronsted acid solution, such as phosphoric or sulfuric acid, to obtain of niobium oxo compounds, such as niobium oxo phosphate or niobium oxo sulfate, respectively. As used herein, the term Bronsted acid refers to a species that can donate a proton, which can then increase the hydronium concentration in solution. In certain embodiments, hydrofluoric acid can also be used. In certain embodiments, the niobium oxo product compounds are present in an aqueous suspension or a colloidal suspension. Alternatively, the niobium oxo compounds are present as a colloidal sol. In certain instances, it is believed that the niobium oxo compounds present in the colloidal sol are smaller than niobium oxo compounds that may be precipitated from solution, thus having enhanced catalyst properties. In certain embodiments, the niobium oxo nanoparticles obtained by this reaction can be supported on a solid support material such as a form of carbon (such as carbon nanotubes, grapheme, graphite, or activated carbon) or metal oxide having general formula $M_xO_y$, wherein M is selected from the elements of groups IV-B, V-B or VI-B of the periodic table or a mixture of thereof; or co-precipitated with other metals such as Tantalum, Tungsten, Zirconium and others. Alternatively, the solid support material can be selected from silica or alumina. Alternatively, the solid support material can be a water insoluble inorganic phosphate, such as phosphates of Mg, Ca, Sr, Al or Zr. Alternatively, the solid support material can be a clay or zeolite material.

In certain embodiments, the catalyst nanoparticles have a diameter of less than about 250 nm, alternatively less than about 200 nm in diameter, or alternatively less than about 100 nm in diameter. In other embodiments, the catalyst nanoparticles have a diameter of between about 10 and 50 nm, alternatively between about 25 and 75 nm, alternatively between about 50 and 100 nm, alternatively between about 30 and 120 nm. In certain embodiments wherein a support is utilized, the support material can have a diameter of at least about 30 µm, alternatively at least about 50 µm alternatively between about 50 and 150 µm, alternatively between about 50 and 100 µm, alternatively between about 100 and 150 µm. In certain embodiments, the support material can have a surface area of at least about 50 $m^2/g$, alternatively between about 50 and 1500 $m^2/g$, alternatively between about 50 and 500 $m^2/g$, alternatively between about 250 and 750 $m^2/g$, alternatively between about 500 and 1000 $m^2/g$, alternatively between about 1000 and 1500 $m^2/g$.

The amorphous hydrated niobium oxide nanoparticle containing catalysts described herein are typically suspended in an aqueous solution or are present in colloidal form, allowing for the catalysts to be used for olefin hydration reactions in the liquid phase, without the catalysts undergoing a corresponding substantial loss of catalytic activity. Niobium oxide materials having an amorphous structure can be prepared according to the methods provided herein, although in certain embodiments the methods may also result in the preparation of a niobium oxide nanoparticle product having at least a partial crystalline structure. Amorphous niobium oxide nanoparticles are believed to have higher acidity in terms of both acid site density and acid strength, as compared with the crystalline form of niobium oxide nanoparticles. In certain embodiments, the amorphous form of niobium oxide is thus preferred. As the crystalline form of the niobium oxide nanoparticles can be obtained after treatment at high temperature, typically at treatment temperatures of at least about 550° C. for niobium oxide nanoparticles obtained from niobic acid, in certain embodiments it is desirable to maintain relatively low temperatures during the preparation of the niobium oxide nanoparticles in an effort to maintain complete, or alternatively a high percentage of, the amorphous structure in the nanoparticles. In certain embodiments, wherein the niobium oxide nanoparticles have been prepared from phosphoric or sulfuric acid, the temperature at which the crystalline form of the niobium oxide nanoparticles forms may be different. In certain embodiments, one advantage of the catalysts described herein is that the catalysts can be regenerated, typically by oxidizing the catalyst by contacting with an acid or subjecting the catalyst to some other oxidative treatment. In certain embodiments, regeneration of the catalyst in the presence of a strong acid, such as $H_3PO_4$ or $H_2SO_4$, helps to maintain the amorphous structure of the niobium oxide nanoparticles, thus preventing the formation of crystalline niobium oxide. An additional advantage of the catalysts described herein is that disintegration or breaking up of the catalysts, due to the use in a liquid phase under high pressure, is typically avoided, as opposed to what is typically encountered with conventional solid inorganic catalysts.

In one embodiment of the present invention, an amorphous hydrated niobium oxide nanoparticle containing catalyst is proposed for use in the hydration of mixed olefins to mixed alcohols, for example the hydration of mixed butenes into mixed butanols. In certain embodiments, the catalyst can be prepared by reacting niobium containing compounds, such as niobium alkoxides (e.g., niobium ethoxide) or niobium halides (e.g., niobium pentachloride or niobium pentabromide), in an acid solution, (preferably a strong Bronsted acid, for example, phosphoric acid or sulfuric acid) to produce niobium oxo phosphate ($NbOPO_4$) or niobium oxo sulfate ($NbOSO_4$) particles, respectively, to further increase acidity of the catalyst (i.e., the acidity of the acid treated catalyst is greater than that of the catalyst that has not been treated with the acid). Nanoparticles of the niobic acid catalyst that have been precipitated by the method described above can also be impregnated onto various solid support or mixtures thereof, such as, silica, alumina, clays, zeolite materials, insoluble metal phosphates (such as those based upon Mg, Ca, Sr, Al or Zr phosphates), metal oxides (having the general formula $M_xO_y$, wherein M is a metal selected from groups IV-B, V-B or VI-B of the periodic table, such as titanium dioxide), or a carbon based compounds (such as carbon nanotubes, grapheme, graphite, or activated carbon). In other embodiments, the nanoparticle niobic acid catalyst can also be co-precipitated with other metal compounds, such as zirconium, titanium, tantalum, vanadium, tungsten, molybdenum, silicon, aluminum or other metals, or metal oxides thereof, including combinations thereof, to form mixed nanoparticle catalyst systems of hydrated niobium acid with other metal oxides.

In certain embodiments of the present invention, the hydrated niobium oxide catalyst nanoparticles can be prepared as follows.

A niobium compound (for example, ammonium niobate (V) oxalate, niobium (III) chloride 1,2-dimethoxyethane, niobium halides, niobium alkoxide, niobium (V) acetyl acetonate, or an alkali metal niobate, such as potassium niobate) is first dissolved in a solvent in which it is soluble to produce a niobium containing solution. Exemplary solvents can include water, organic acids (such as formic acid, acetic acid, and perfluoro acetic acid) or alcohols (such as methanol, ethanol, propanol, or butanol). Preferably, the concentration of niobium metal in the solution is between about 0.01 mol/L and 10 mol/L; alternatively between about 0.1 mol/L and 1 mol/L; alternatively between about 0.5 mol/L and 2 mol/L; alternatively between about 0.5 mol/L and 1.5 mol/L. As used herein, niobium compounds refers to compounds that are able to donate niobium. In certain embodiments, niobium pentachloride or a niobium alkoxide, such as niobium ethoxide, is used as a niobium source. In certain preferred embodiments, niobium alkoxide (Nb(OR)$_5$) can be used, wherein R denotes a straight chain or branched alkoxy group that can be used, preferably an alkoxy group having fewer than about 6 carbon atoms, more preferably fewer than 4 carbon atoms. In certain embodiments, the alkoxy group is selected from the group consisting of ethoxy, propoxy, iso-propoxy, butoxy, 2-butoxy, and t-butoxy groups, and mixtures thereof. Without wishing to be bound by theory, it is believed that as the number of carbon atoms present in the alkoxy group increases, the reactivity of the precursor in the hydrolysis and condensations reactions decreases.

The niobium containing solution can then be added drop wise into water or into an aqueous acid solution (e.g., phosphoric acid or sulfuric acid) in a mixing step and maintained under constant stirring for up to about 5 minutes, alternatively up to about 10 minutes, alternative up to about 15 minutes, or greater. When an aqueous acid solution is used, the concentration can be in the range of between about 0.01M and 5M, alternatively between about 0.011\4 and 1M, alternatively between about 0.5M and about 2.5M, alternatively between about 1M and 3M, alternatively between about 2M and 5M. The acids can be used either singly or in combination. In certain embodiments, the temperature during the mixing step is on the order of between about 40° C. and 80° C., alternatively between about 40° C. and 60° C., alternatively between about 45° C. and 65° C., or alternatively between about 50° C. and 80° C.

In certain embodiments, the temperature during the mixing step is maintained at a temperature of less than about 80° C. to prepare a colloidal sol. In certain embodiments, the temperature is maintained at a temperature of greater than about 80° C. to produce solid niobium precipitates. In certain embodiments, a precipitating agent, such as ammonia, can be added to induce precipitation of the niobium oxide compounds.

After the mixing step has been completed and drop wise addition of the niobium containing solution has been completed, the resulting mixture can then be heated to a temperature that is sufficiently high to allow the solution to boil to form a niobium oxide compound and the solution can be maintained at the boiling point for at least for about 10 minutes, alternatively between about 5 and 15 minutes, or alternatively between about 10 and 30 minutes, or greater.

The hydrated niobium oxide solution can then be washed several times with deionized water, optionally with agitation, to facilitate the removal of any remaining phosphoric or sulfuric acid. The washing steps can optionally be carried out repeatedly, to ensure that phosphoric or sulfuric acid will be removed sufficiently. The wash water can optionally be removed by rotary evaporation. In certain embodiments, removal of the wash water is performed at temperatures that do not exceed about 80° C. to ensure maintenance of the product as a colloidal sol, rather than forming a precipitate.

Butenes are only sparingly soluble in water, and thus tend to form separated phases under the certain reaction conditions, particularly in environments wherein butenes are used in sufficiently large quantity. As butanol is relatively non-polar, it has a favorable distribution in the reaction as a significant amount of the butanol molecules formed are expected to be present in the butene-rich organic phase, assisting in separation thereof. Thus, in certain embodiments, the simultaneous extraction of the butanols during the course of the reaction (i.e., the hydration of butenes to butanols) might help shift the reversible reaction in the forward direction. Similarly, in the hydration of other olefins, the alcohols produced thereform can be removed during the reaction as they are formed.

The hydrated niobium oxide nanoparticles described herein maintain a relatively high catalytic activity, which may be due in part to its higher intrinsic effective acidity, in terms of number of the total number of acid sites present, which can be maintained in both highly polar and protic media.

In certain embodiments of the present invention, mixed butenes, which can be obtained from an FCC process product stream or from a product stream from another cracking process, optionally including propylene or LPG, can be simultaneously hydrated with water in the presence of the niobium oxide nanoparticle containing catalysts described herein to produce sec-butyl alcohol, tert-butyl alcohol and isopropanol. Unconverted olefins can be separated by known means and re-cycled to the dehydrogenation section.

As noted previously, hydration of olefins to alcohols (such as butenes to butanols) is typically an acid catalyzed reaction, requiring strong acids to achieve desired reaction kinetics. Strong liquid acids, for example sulfuric acid, are typically used in conventional butene hydration processes. Sulfuric acid, however, becomes diluted, and must then be reconcentrated before it can be recycled to the process. Additional problems associated with using such liquid acid catalysts, which are not encountered when using the niobium oxo containing catalysts described herein include, problems with the separation and recovery of the liquid catalyst, corrosion of equipment and installations contacting the catalyst, and the formation of undesired byproducts, such as secondary butyl ether, isopropyl alcohol, $C_5$-$C_8$ hydrocarbons, and polymers formed during the hydration.

Solid acid catalysts, such as cationic exchange resins, typically do not suffer the same disadvantages suffered by liquid acid catalysts, and frequently offer substantial reaction rates in both polar and non-polar media. These catalyst resins, however, also have disadvantages as they have been found to suffer from a leaching tendency and their limited range of applications. Additionally, sulfonic acid groups present can be irreversibly liberated from the resin as it becomes deactivated. Deactivated catalytic resins also suffer that they cannot be regenerated by calcination, which is commonly employed for the regeneration of inorganic solid catalysts.

In certain embodiments of the present invention, butanols prepared by the hydration of mixed butenes with the niobium based nanoparticle catalysts described herein have good gasoline blending octane characteristics and may be used in combination (i.e., a combination of butanols) as certain petroleum additives, as shown in Table 1 below.

In an exemplary process, a system is provided for the catalytic hydration of olefins. The system can include a closed reactor suitable for operation at elevated temperatures and pressures that can be charged with the solid acidic catalyst described herein. An olefin feedstock and water are each separately fed to the reactor, where the olefin feedstock undergoes hydration in the presence of the catalyst to produce a product stream which includes an alcohol. The product stream can be supplied to a separation unit where the product stream can be separated into an organic phase and an aqueous phase, wherein the phases can be worked up by known methods. Unreacted olefin feedstock that is separated from the produced alcohol can be recycled to the reactor.

In certain embodiments of the present invention, an entire butene fraction containing one or more of 1-butene; 2-trans-butene, 2-cis-butene and isobutene can be supplied to a reaction vessel and hydrated to sec-butanol and tert-butanol using niobic acid nanoparticle catalysts prepared by according to the methods described herein. The remaining unconverted butenes can be separated by known means and recycled back to the hydration process.

TABLE 1

Properties of Butanols as compared to Gasoline

| Fuel | Energy Density | Air-Fuel Ratio | Specific Energy | Heat of Vaporization | RON | MON |
| --- | --- | --- | --- | --- | --- | --- |
| Gasoline | 32 | 14.6 | 2.9 | 0.36 | 91-99 | 81-89 |
| Butanols | 29.2 | 11.1 | 3.3 | 0.43 | 96-110 | 78-99.5 |

Example 1

Catalyst A

A solution containing approximately 5.15 g of Nb(EtO)$_5$ in about 100 mL of EtOH was added drop wise to a solution containing about 0.093 g of $H_3PO_4$ (approximately 85% by wt.) in 500 mL of deionized water (i.e., a molar ratio Nb:$H_3PO_4$ of about 20:1). The addition was done at room temperature and constant stirring (about 800 rpm). After the addition of the niobium containing solution was finished, the temperature of the mixture was increased until the mixture boiled, and the boiling was maintained for about half an hour. After cooling to room temperature, the final solution was evaporated using a rotary evaporator (removing ethanol and a portion of the water) to produce a milky white aqueous solution. The solution was washed with deionized water several times until a pH of the wash water of between about 5 and 6 was reached and the wash water was removed by rotary evaporation. The resulting milky solution (yield: between about 1 to 1.5 g) was then used without further evaporation or removal of the water.

Example 2

Catalyst B

To a solution containing approximately 4.25 g of NbCl$_5$ in about 70 mL of deionized water was added drop wise a solution containing about 3.57 g of $H_3PO_4$ (approximately 85% by wt) and about 100 mL of deionized water (i.e., a molar ratio Nb:$H_3PO_4$ of about 1:2) at room temperature and under constant stirring. The resulting solution was stirred at room temperature for approximately 60 minutes. To this solution an aqueous ammonia solution (1 M) was added drop wise until a pH of about 5 was obtained and a solid precipitate was formed. The precipitate was filtered and washed several times yielding between about 1.5 and 4 g, depending upon the amount of water present in the precipitate.

Example 3

Catalyst C

A solution containing approximately 7 g of Nb(EtO)$_5$ in about 100 mL of EtOH was added drop wise to a solution containing about 51 g of $H_2SO_4$ in about 500 mL of deionized water (i.e., a molar ratio Nb:$H_2SO_4$ of about 20:1). The addition is done at room temperature and under constant stirring (about 800 rpm). After the addition was completed, the resulting solution was heated to boiling and maintained at a boil for about half an hour. After cooling to room temperature, the final solution was evaporated with a rotary evaporator, and the resulting solid product was washed several times until a pH of the wash water of between about 5 and 6 was obtained. The precipitate was filtered and washed several times yielding between about 3 and 5 g, depending upon the amount of water present in the precipitate. The obtained precipitate was then used in the hydration test.

Example 4

Butene Hydration

In four separate tests, approximately 200 g of deionized water and 4 g of the exemplary acid catalysts A, B and C (prepared according to the examples above), and comparative catalyst Amberlyst 15, were placed in a Parr autoclave, which was then sealed and purged with nitrogen five times at about 50 Psi. The concentration of the solution of acid catalyst A was estimated based upon starting material. Approximately 10 mL of pure 2-trans-butene was then introduced into the autoclave under 50 psi of nitrogen gas. The autoclave was then heated to a temperature of about 150° C. and maintained at this temperature for a period of 3 hours. After 3 hours, heating was discontinued and the autoclave was allowed to return to room temperature over a period of about 2 to 3 hours, and the excess pressure in the system was vented. The autoclave was then opened and the reaction mixture recovered. The conversion rates were determined by means of gas chromatography. All catalysts showed a selectivity to sec-butanol with trans-2-butene. The conversion rates of different hydration conditions are listed in Table 2.

TABLE 2

Hydration of 2-Butene.

| Catalyst | $H_2O$ (mL) | Butene (mL) | Acid (g) | Conversion (%) |
| --- | --- | --- | --- | --- |
| A | 200 | 10 | 4 | 0.13 |
| B | 200 | 10 | 4 | 0.47 |
| C | 150 | 10 | 4 | 0.92 |
| Amberlyst 15 (comparative) | 150 | 10 | 4 | 0.82 |

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

That which is claimed is:

1. An olefin hydration catalyst comprising a solid support material having niobium oxo sulfate or niobium oxo phosphate nanoparticles precipitated thereon.

2. The catalyst of claim 1, wherein the solid support material upon which the nanoparticles are precipitated is selected from the group consisting of silica, alumina, metal oxides of groups IV-B, V-B or VI-B of the periodic table, inorganic phosphates, carbon nanotubes, grapheme, activated carbon, and combinations thereof.

3. The method of claim 1, wherein the solid support material upon which the nanoparticles are precipitated is selected from the group consisting of zirconium, titanium, tantalum, vanadium, tungsten, molybdenum, silicon, aluminum, or combinations thereof.

4. The method of claim 1, wherein the nanoparticles have an amorphous crystal structure.

5. The method of claim 1, wherein the nanoparticles have a crystalline crystal structure.

6. The method of claim 1, wherein the nanoparticles have diameter of less than about 100 nm, and the support material has a diameter of between about 50 and 150 μm.

7. A method of preparing the catalyst of claim 1, the method comprising the steps of:

contacting a niobium containing salt compound with a Bronsted acid and allowing a precipitate to form;
removing excess liquid; and
recovering a solid catalyst material.

8. The method of claim 7, further comprising the step of contacting the niobium containing compound and the Bronsted acid in the presence of a support material and allowing the catalyst nanoparticles to deposit on the surface of the support material.

9. The method of claim 8, wherein the support material is selected from the group consisting of silica, alumina, metal oxides of groups IV-B, V-B or VI-B of the periodic table, inorganic phosphates, carbon nanotubes, grapheme, activated carbon, and combinations thereof.

10. The method of claim 8, wherein the support material is selected from the group consisting of zirconium, titanium, tantalum, vanadium, tungsten, molybdenum, silicon, aluminum, or combinations thereof.

11. The method of claim 7, wherein the Bronsted acid is selected from the group consisting of sulfuric acid and phosphoric acid.

12. The method of claim 7, wherein the niobium containing compound is a niobium alkoxide.

13. The method of claim 7, wherein the niobium containing compound is a niobium (V) halide.

14. A method for the hydration of an olefin to an alcohol, the method comprising the steps of:

contacting an olefin feedstock with the catalyst of claim 1 in a reaction zone for a contact time sufficient to convert at least a portion of the olefin present into an alcohol;
withdrawing a product stream from said reaction zone, said product stream comprising an organic phase and an aqueous phase, the organic phase comprising the alcohol; and
separating the organic phase to produce an alcohol product stream.

15. The method of claim 14, wherein the olefin feedstock comprises a mixture of butanes.

16. The method of claim 14, wherein the alcohol comprises mixed butanols.

17. The method of claim 14, wherein the olefin feedstock is selected from the group consisting of an FCC refinery propylene stream, gas plant off-gases, FCC light gasoline stream, and a product stream or off-gas stream from any other thermal cracking unit.

18. The method of claim 14, further comprising the step of separating unreacted olefin from the organic phase and recycling the unreacted olefin to the reaction zone.

* * * * *

UNITED STATES PATENT AND TRADEMARK OFFICE
CERTIFICATE OF CORRECTION

PATENT NO. : 8,629,080 B2
APPLICATION NO. : 13/052812
DATED : January 14, 2014
INVENTOR(S) : Abdennour Bourane, Stephan Ralf Vogel and Wei Xu It is certified that error appears in the above-identified patent and that said Letters Patent is hereby corrected as shown below:

In the Claims

In Column 10, Line 37, Claim 15, the second word appears as "butanes" and should read --butenes--.

Signed and Sealed this
Eighth Day of September, 2015

Michelle K. Lee
*Director of the United States Patent and Trademark Office*